United States Patent [19]

Horvath et al.

[11] Patent Number: 5,354,916

[45] Date of Patent: Oct. 11, 1994

[54] LOW TEMPERATURE CONVERSION OF ALKANES

[75] Inventors: Istvan T. Horvath, New Hope, Pa.; John M. Millar, Summit; Raymond A. Cook, Hampton, both of N.J.

[73] Assignee: Exxon Research and Engineering Company, Florham Park, N.J.

[21] Appl. No.: 187,351

[22] Filed: Jan. 24, 1994

Related U.S. Application Data

[63] Continuation of Ser. No. 10,039, Jan. 28, 1993, abandoned, which is a continuation-in-part of Ser. No. 848,814, Mar. 10, 1992, abandoned.

[51] Int. Cl.$^5$ .................. C07C 29/58; C07C 17/10
[52] U.S. Cl. .................. 568/893; 570/254; 570/261; 570/168; 570/174
[58] Field of Search ............ 568/893; 570/254, 261, 570/168, 174

[56] References Cited

U.S. PATENT DOCUMENTS

| | | | |
|---|---|---|---|
| 4,523,040 | 6/1985 | Olah | 568/671 |
| 4,746,760 | 5/1988 | Bergman et al. | 570/241 |
| 4,849,534 | 7/1989 | Bergman et al. | 556/23 |

OTHER PUBLICATIONS

Kushch et al, "Kinetics and Mechanism of Methane Oxidation in Aqueous Solutions of Platinum Complexes", Nouveau J. de Chemie, 729 (1983).

Gol'dshleger et al, "Reactions of Alkanes in Solutions of Chloride Complexes of Platinum", Russian J. of Phys. Chem., 46(5) 785, 1971.

Shilov et al, "Activation of Saturated Hydrocarbons by Metal Complexes In Solution", Coordination Chemistry Reviews, 24 (1977) 97–143.

Olah et al, "Selective Monohalogenation of Methane over Supported Acid or Platinum Metal Catalysts and . . .", J Amer Chem Soc, 107 (24) 7097 (1985).

*Primary Examiner*—Howard T. Mars
*Attorney, Agent, or Firm*—Linda M. Scuorzo

[57] ABSTRACT

The invention relates to a process for selectively producing alkyl halides from alkanes, such as methane and ethane at low temperatures and low pressures. Optional hydrolysis to the corresponding alcohols may follow. The process involves adding an alkane and an added halogen source to an aqueous solution in a homogeneous system in the presence of a transition metal halide containing complex, for a time, under conditions and in effective amounts that will permit the formation of alkyl monohalides.

7 Claims, No Drawings

LOW TEMPERATURE CONVERSION OF ALKANES

This application is a continuation of application Ser. No. 08/010,039, filed Jan. 28, 1993, which is a continuation-in-part of application Ser. No. 07/848,814 filed Mar. 10, 1992, both now abandoned.

BACKGROUND OF THE INVENTION

1. Field of the Invention

The invention relates to a process for the selective monohalogenation of alkanes to alkyl monohalides in a homogeneous (supported or unsupported) liquid phase system under mild conditions of temperature and pressure. The halogenation may be followed by hydrolysis to produce alcohols.

2. Description of Related Art

Selective halogenation of alkanes to alkyl halides, particularly chlorination to alkyl chlorides under relatively mild temperature and pressure offers the possibility for development of simple, low cost means for producing alkyl halides. Alkyl halides are known to those having ordinary skill in the art to have utility as a feedstock for more valuable commercial reactions. For example, methyl chloride and other alkyl halides have utility as an intermediate for production of alcohols, such as methanol, which itself is useful as an alternative, less environmentally damaging, fuel source. Additionally, methanol can be used as a feedstock for chemical reactions; for example, it can be used in reactions to yield gasoline or other hydrocarbons. More importantly, alcohol can be used as a transportation fuel source or as an additive to transportation fuels, particularly gasoline, to reduce hydrocarbon emissions and produce a more environmentally safe fuel.

The literature describes a number of processes for monohalogenating alkanes. However, unlike the processes described in the literature, applicants' monohalogenate alkanes in a process that uses a homogeneous liquid phase/transition metal complex system that uses no metal-bound halogen sources operates in the presence of the transition metal halide complexes, shows no evidence of metallic platinum formation during the reaction until the added halogen source is depleted, and is highly selective for monohalogenated products and their hydrolysis products.

SUMMARY OF THE INVENTION

The present invention relates to a process for selectively producing alkyl monohalides, particularly alkyl chlorides, at relatively mild conditions of temperature and pressure in a homogeneous system from alkanes, particularly methane and ethane and mixtures thereof, by combining the alkane and an added halogen source in an aqueous solution, preferably water, in the presence of a soluble transition metal halide complex. The alkyl monohalides may be converted via hydrolysis to alcohols.

DESCRIPTION OF THE INVENTION

Alkyl halides, particularly alkyl chlorides such as methyl chloride, can be produced selectively by a process which comprises adding an alkane or mixtures of alkanes, and an added halogen source to an aqueous solution in the presence of a transition metal halide complex. The alkanes suitably may be methane, ethane or higher alkanes. The halogens are preferably chlorine, fluorine or bromine. The corresponding alcohol(s) may be produced during the reaction from the hydrolysis of the resulting alkyl halides or in a separate hydrolysis step.

The transition metal halide complex can be added to the system or may be produced by one ordinarily skilled in the art, in situ, from a compound consisting of a transition metal and a ligand capable of reacting to form the complex provided that the resulting complex is homogeneous with the system. Particularly useful transition metal halide complexes are those in which the transition metal is platinum, palladium, and nickel or mixtures thereof or, more preferably, platinum; and the halide is fluoride, chloride, bromide, or iodide or mixtures thereof, preferably chloride. The preferable combination of transition metal and halide is that of platinum and chloride; for example, as $(PtCl_4)^{-2}/(PtCl_6)^{-2}$ or as $(PtCl_4)^{-2}$ alone. The cation portion of the complex may be a Group IA or IIA element, preferably $H^+$, $K^+$, or $Na^+$. The particular complex may be prepared by methods known to ones ordinarily skilled in the art or obtained from commercial sources. The complex should be homogeneous with the aqueous solution in the system.

The complex useful in the process of the present invention and the aqueous solution also may be supported in a solid hydrophilic support. In general, the support will be a porous solid material. For example, materials having a pore volume relative to solid weight of from about 0.1 to 1.5 cubic centimeters per gram, with a preferred range of from about 0.4 to 1.0 are especially useful supports. The macropore volume of the porous support should be at least 10% of the total pore volume. By macropore volume is meant pores having diameters greater than 100 Angstroms.

Specific examples of such materials useful as a support for the homogeneous liquid phase system in the practice of the process of the present invention are silica, clay, alumina, silica/alumina, acid treated clay and titania. Indeed, it is particularly preferred in the practice of the present invention to use acidic porous support materials such as silica/alumina, clay and, even more particularly, acid treated clay.

In a supported homogeneous liquid phase system, the transition metal complex used in the process of the present invention is dissolved in a supported aqueous acid phase; i.e., an aqueous acid phase that does not circulate or flow as a liquid, but is immobile and supported by the porous solid support. Typical supported aqueous acid liquid phase materials that may be used in the practice of the present invention include aqueous solutions of HCl, HF, $CH_3COOH$, $CF_3COOH$, $H_3PO_4$, $H_2SO_4$, $CH_3SO_3H$, $CF_3SO_3H$, $BF_3$ and mixtures thereof, preferably HCl, HF and mixtures thereof.

The volume of the supported aqueous phase will generally be a predetermined maximum amount that can be supported without causing the particles of the support to stick together, which amount may readily be determined by one ordinarily skilled in the art. The amount of aqueous phase should be less than that of the pore volume of the specific support employed. Indeed, it is preferred that the amount of aqueous phase will be about 10% less than the pore volume of the support. Thus, for example, about 1.3 cc of aqueous phase will be used with a support having a pore volume of 1.5 cc/gm.

Finally, in the homogeneous liquid phase system used in the process of the present invention, there is included a transition metal halide complex which is dissolved in the aqueous phase. The transition metals that may be employed herein include cobalt, rhodium, iridium, palladium, platinum, ruthenium, rhenium and mixtures thereof, but preferred is platinum.

In preparing a supported homogeneous liquid phase system, the transition metal complex is first dissolved in the aqueous phase, then the solution is impregnated into the porous support material by any appropriate means known to one skilled in the art, for example, by the incipient wetness technique.

The added halogen source used in the practice of the present invention should be additional to any halide contained in the transition metal halide complex having the transition metal halide. The source may be any Group VIIA element or compound, any Group VIIA-containing compound, and any other Group VIIA-containing species that exist(s) as an equilibrium product of the reaction of the Group VIIA element, compound or Group VIIA-containing species in water in the presence of the complex and mixtures thereof. The added halogen source may be in elemental, molecular, ionic, free radical, other form or species, or mixtures thereof that are consistent with the chemical composition of the source. It may be introduced into the system in gaseous, liquid or other form that is or becomes soluble or dissolves in whole or in part in water, or it may be present in the system as an equilibrium product of the reactions involved in the particular system. The added halogen source is preferably a halogen, halide and hypohalide, or mixtures thereof, more preferably chlorine, a chloride and a hypochloride; even more preferably, $Cl_2$ and HOCl, most preferably $Cl_2$.

In the process of the present invention, monohalogenation of the alkanes is carried out under relatively mild conditions. Suitable monohalogenations may be carried out at a temperature range from about 20° C. to about 315° C., preferably from about 20° C. to about 200° C., more preferably from about 25° to about 150° C.; and hydrolysis to the corresponding alcohols may be accomplished at temperatures from about 20° C. to about 315° C., preferably from about 100° C. to about 250° C., more preferably from about 100° C. to about 150° C. The total pressure selected will vary based on the form in which the alkane and added halogen source are introduced into the system (e.g. liquid, gas), but generally for gaseous sources should be from about 1 atm to about 300 atm. Where, for example, the reaction is carried out using gaseous $Cl_2$ at about 20° C. to about 25° C., the preferable pressure range is from about 1 to about 6 atm. Halogenation of alkanes to alkyl monohalides, according to the process of the present invention, may be carried out selectively, using the ratio of added halogen source to alkane of greater than or equal to about 1:1, preferably from about 1:1 to about 1:10, more preferably from about 1:1 to about 1:100.

If a significant amount of alcohol production is desired the reaction should be permitted to progress for a sufficient time to produce alcohol, but should not be allowed to proceed to the point that the added halogen source is depleted. The reactants should be used in effective amounts for the production of the alkyl halide. Where the added halogen source is $Cl_2$ or HOCl and the complex containing the transition metal halide is $Na_2PtCl_4/Na_2PtCl_6$ or $Na_2PtCl_4$ alone, the process produces alkyl chlorides, particularly methyl chloride and ethyl chloride in high selectivity at pressures as low as about 5 atm, and at temperatures as low as about 100° C. almost immediately. The reaction may be expected to proceed slowly, even at pressures as low as 1 atm.

In all cases, the pressure and temperature of the reaction and concentrations of reactants should be such that the flash point of the gaseous reactants is not exceeded. Due regard should be given to the corrosive nature of the particular Group VIIA reactants used. Particularly in the case of fluorination of alkanes, reactions should be performed in high dilution, preferably in the presence of an inert gas, to minimize handling problems. For processes known to those ordinarily skilled in the art for carrying out reactions using halogens, see e.g., F. Cotton and G. Wilkinson, *Advanced Inorganic Chemistry. A Comprehensive Text*, 4th ed., Part 2, Ch. 17, p.p. 542–576 "The Group VII Elements, Fluorine, Chlorine, Bromine, Iodine and Astatine".

The process of the present invention may be run in batch or may be operated continuously. The latter may be accomplished by removing on an ongoing basis the alkyl monohalides (or the alcohol, if the reaction is allowed to proceed under conditions which result in the hydrolysis to alcohol), recycling the complex containing the transition metal halide and regenerating the halogen source by oxidation of the halogen containing by-products of the reaction.

Reaction times for the process of the present invention will depend on the particular combination of reagents used, the sample size, and the type of process (batch or continuous), but should be sufficient to permit the synthesis of alkyl monohalides, and, if alcohol production is desired, the hydrolysis of the alkyl monohalides to alcohol. In order to maintain the selectivity of the reaction toward the production of alkyl monohalides, care should be taken such that the added halogen source is not depleted.

Subject to the foregoing limitations, reaction times generally needed to produce alcohol in quantities that are equal to or greater than those of, for example, alkyl chloride, are from about 15 minutes to about 16 hours at from about 100° C. to about 150° C. and from about 20 atm to about 80 atm, the more preferable time being from about 30 minutes to about 8 hours.

The selection of the particular reaction times, conditions and combination and concentrations of reagents will be readily apparent to one ordinarily skilled in the art given parameters established by the the teachings herein. General background concerning, for example, the conditions necessary for the chlorination of methane can be found in J. S. Sconce, *Chlorine, Its Manufacture, Properties and Uses*, R. Landau and S. Fox, Chapter 12, "Chlorinated Methanes", pp. 334 to 375. Other halogenation reactions may be carried out similarly by one ordinarily skilled in the art.

In order to maintain the high selectivity for alcohol production that is a characteristic of the present invention, it is important that the added halogen source not be depleted during the reaction. This may be accomplished by oxidizing the halide and oxyhalide by-products of the reaction to regenerate gaseous halogen and recycling them back into the system, or by adding additional halogen source to the reaction. Otherwise, at the point at which the added halogen source is depleted, the reaction may continue for a time and is identified by the formation of the metallic (zero valence) form of the transition metal portion of the complex (e.g., metallic platinum for the $Na_2PtCl_4/Na_2PtCl_6$ complex). It should be emphasized that in order to carry out chlorination, the platinum complex is required in a concentration of from about 0.001 mole/liter to about 1 mole/liter, preferably from about 0.01 mole/liter to about 1 mole/liter, more preferably from about 0.1 mole/liter to about 0.5 mole/liter. However, in order to carry out the hydrolysis step, the platinum complex in a concentration of from about 0.01 mole/liter to about 1 mole/liter is required.

The following examples are illustrative and not intended to limit the scope of the invention.

EXAMPLE 1

Commercially available chlorine, methane, $Na_2PtCl_4$ and $Na_2PtCl_6$ were used without further purification. The reaction was performed at 125° C. for 2 hours in an 8 ml sapphire high pressure nuclear magnetic resonance ("NMR") tube with 3 g of a $D_2O$ solution containing 1.2 mmol $Na_2PtCl_6$ and 0.16 mmol $Na_2PtCl_4$ at 72 psi $Cl_2$ and 392 psi $^{13}CH_4$. For an illustration of a sapphire NMR tube assembly, see I. T. Horvath and E. Ponce, "New Valve Design for High Pressure Sapphire Tubes for NMR Measurements", *Review of Scientific Instruments*, Vol. 62, No. 4, pp. 1104–1105 (1991). After 2 hours, the high pressure NMR spectrum showed the selective formation of methanol (approximately 40%, in the form of $CH_3OD$) as evidenced by the peak at about 49.5 ppm. NMR indicates the formation of trace amounts of $CO_2$, with a peak at about 125 ppm; $CH_2(OD)_2$ (approximately 2%), with a peak at about 85 ppm; $CH_2Cl_2$ (approximately 2%) with a peak at about 56 ppm; $CH_3Cl$, (approximately 5%) with a peak at about 26 ppm; and unreacted methane (approximately 50%), with a peak at about −4 ppm. Formation of metallic platinum was not observed upon visual inspection of the transparent NMR tube under pressure. HCl that is formed as a by-product during the formation of methanol may be treated with $O_2$ to recover the chlorine. Methanol may be separated by distillation by processes known to one having ordinary skill in the art.

EXAMPLE 2

Commercially available methyl chloride was used without further purification. Hydrolysis was carried out in a sapphire high pressure NMR tube with 3 g of a $D_2O$ solution containing 1.2 mmol $Na_2PtCl_6$ and 0.16 mmole $Na_2PtCl_4$ at 50 psi $CH_3Cl$ and heated to 125° C. for 1 hour. High pressure $^{13}C$ NMR spectrum showed the selective formation of methanol (in the form of $CH_3OD$). The spectrum had the following characteristics: a peak at about 49.5 ppm, representing $CH_3OD$ (approximately 49%); a peak at about 26 ppm for $CH_3Cl$ (approximately 50%).

What is claimed is:

1. A process for selectively making alkyl monochlorides and hydrolysis products which comprises: forming a homogeneous liquid phase containing water, an alkane, a soluble transition metal halide complex which is $(PtCl_4^{-2})/(PtCl_6)^{-2}$ and an added halogen source selected from the group consisting of chlorine, a chloride and a hypochloride in addition to that contained in the transition metal; reacting the alkane, the added halogen source and the transition metal halide complex at a temperature and for a time and in amounts that are effective to produce the corresponding alkyl monochloride and hydrolysis products without the formation of metallic platinum wherein the added halogen source is not completely depleted.

2. The process of claim 1 wherein the ratio of added halogen source to alkane is greater than or equal to about 1:1.

3. The process of claim 1 wherein the ratio of added halogen source to alkane is from about 1:1 to about 1:10.

4. The process of claim 1 wherein the ratio of added halogen source to alkane is from about 1:1 to about 1:100.

5. The process of claim 1 wherein the added halogen source is a gas.

6. The process of claim 1 wherein the added halogen source is $Cl_2$.

7. The process of claim 1 wherein the temperature is in a range from about 20° C. to about 315° C.

* * * * *